United States Patent
Krasutsky et al.

(10) Patent No.: US 6,634,575 B2
(45) Date of Patent: Oct. 21, 2003

(54) BIRCH BARK PROCESSING AND THE ISOLATION OF NATURAL PRODUCTS FROM BIRCH BARK

(75) Inventors: Pavel A. Krasutsky, Duluth, MN (US); Robert M. Carlson, Duluth, MN (US); Vitaliy V. Nesterenko, Duluth, MN (US); Igor M. Kolomitsyn, Duluth, MN (US); Chris F. Edwardson, Duluth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/938,173

(22) Filed: Aug. 23, 2001

(65) Prior Publication Data

US 2002/0043577 A1 Apr. 18, 2002

Related U.S. Application Data

(62) Division of application No. 09/371,298, filed on Aug. 10, 1999.

(51) Int. Cl.⁷ ............................................... B02C 19/12
(52) U.S. Cl. ........................................ 241/19; 241/28
(58) Field of Search .............................. 241/28, 30, 19

(56) References Cited

U.S. PATENT DOCUMENTS

| | | |
|---|---|---|
| 3,826,433 A | 7/1974 | Erickson et al. |
| 3,981,453 A | 9/1976 | Berlyn et al. |
| 4,732,708 A | 3/1988 | Ekman et al. |
| 5,468,888 A | 11/1995 | Bouboutou et al. |
| 5,529,769 A | 6/1996 | Cho et al. |
| 5,577,671 A * | 11/1996 | Seppanen et al. ............ 241/14 |
| 5,658,947 A | 8/1997 | DasGupta et al. |
| 5,679,828 A | 10/1997 | Lee et al. |
| 5,750,709 A | 5/1998 | Castor |
| 5,804,575 A | 9/1998 | Pezzuto et al. |
| 6,260,777 B1 * | 7/2001 | Seppanen ................ 241/119 |

FOREIGN PATENT DOCUMENTS

CA 658673 * 12/1974

OTHER PUBLICATIONS

*Supercritical Fluid Extraction–Principals and Practice, Second Edition*, M.A. McHugh, et al., editors, Butterworth–Heinemann, pp. 1–512, (1994).
*Supercritical Fluid Science and Technology, ACS Symposium Series: 406*, K.P. Johnston, et al., editor, American Chemical Society, pp. 1–550, (1989).
"Betulinic acid found to have strong anticancer activity", 1 p.
Cordeiro, N., et al., "Cork suberin as a new source of chemicals 1. Isolation and chemical characterization of its composition", *International Journal of Biological Macromolecules, 22*, pp. 71–80, (1998).
Eckerman, C., et al., "Comparison of Solvents for Extraction and Crystallization of Betulinol from Birch Waste", *Paperi ja Puu—Papper och Tra, vol. 67, No. 3 (abstract)*, 100, (1985).
Ekman, R., "The Suberin Monomers and Triterpenoids from the Outer Bark of *Betula verrucosa* Ehrh", *Holzforschung, 37*, pp. 205–211, (1983).

(List continued on next page.)

*Primary Examiner*—Mark Rosenbaum
(74) *Attorney, Agent, or Firm*—Schwegman, Lundberg, Woessner & Kluth, P.A.

(57) ABSTRACT

The invention provides methods for separating outer birch bark from inner birch bark. The invention also provides methods for isolating betulin; lupeol; betulinic acid; 9,10-epoxy-18-hydroxyoctadecanoic acid; 9,10,18-trihydroxyoctadecanoic acid; polyphenolic polymers and fatty acids from birch bark.

4 Claims, 10 Drawing Sheets

PRINCIPAL SCHEME OF OUTER AND INNER BARK SEPARATION

OTHER PUBLICATIONS

Fuchino, H., et al., "Chemical Evaluation of Betula species in Japan. II. Constituents of *Betula platyphylla* var.japonica", *Chemical & Pharmaceutical Bulletin (Tokyo)*, 44 (5), pp. 1033–1038, (1996).

Fujioka, T., et al., "Anti–AIDS Agents, 11. Betulinic acid and platanic acid as anti–HIV principles from *Syzigium claviforum* and the anti–HIV activity of structurally related triterpenoids", *Journal of Natural Products*, 57 (2), pp. 243–247, (Feb. 1994).

Fulda, S., et al., "Betulinic acid triggers CD95 (APO–1/Fas)—and p53–independent apoptosis via activation of caspases in neuroectodermal tumors", *Cancer Research*, 57 (21), pp. 4956–4964, (Nov. 1, 1997).

Geles, I.S., "Bark as Fuel", *Bumazh, Prom., No. 4*, Abstract, pp. 21–22, (Apr. 1986).

Jaaskelainen, P., "Betulinol and its utilisation", *Paperi Ja Puu—Papper Och Tra*, 63 (10), pp. 599–603, (Oct. 1981).

Kolattukudy, P.E., "Structure, Biosynthesis, and Biodegradation of Cutin and Suberin", *Annual Review of Plant Physiology*, 32, pp. 539–567, (1981).

Laks, P.E., et al., "Flavonoid Biocides: Wood Preservatives Based on Condensed Tannins", *Holzforschung*, 42, pp. 299–306, (1988).

Lugemwa, F.N., et al., "A Heliothis zea Antifeedant from the Abundant Birchbark Triterpene Betulin", *Journal of Agricultural and Food Chemistry*, 38, pp. 493–496, (Feb. 1990).

Manez, S., et al., "Effect of selected triterpenoids on chronic dermal inflammation", *European Journal of Pharmacology*, 334 (1), pp. 103–105, (Sep. 3, 1997).

Miles, D.H., et al., "Boll Weevil Antifeedants from *Elecharis dulcis* Trin.", *Journal of Agricultural and Food Chemistry*, 42, pp. 1561–1562, (1994).

Nowak, G.A., "Cosmetic and medicinal properties of the birch", *American Perfumer and Cosmetics*, 81, pp. 37–39, (Nov. 1966).

O'Connell, M.M., et al., "Betulin and Lupeol in Bark from Four White–Barked Birches", *Phytochemistry*, 27 (7), pp. 2175–2176, (1988).

Ohara, S., et al., "Utilization of Wood Extractives I. Extractives from the bark of *Betula platyphylla* Sukatchev var. japonica Hara", *Mokuzai Gakkaishi*, 32 (4), pp. 266–273, (1986).

Pearce, R.B., "Suberin in the sapwood of oak (*Quercus robur* L.) its composition from a compartmentalization barrier and its occurrence in tyloses in undecayed wood", *Physiological Plant Pathology*, 24, pp. 71–81, (1984).

Pisha, E., et al., "Discovery of Betulinic Acid as a Selective Inhibitor of Human Melanoma that Functions by Induction of Apoptosis", *Nature Medicine*, 1 (10), pp. 1046–1051, (Oct. 1995).

Pizzi, A., "Wood/Bark Extracts as Adhesives and Preservatives", *Forest Products Biotechnology, Chapter 11*, Dr. Alan Bruce, et al., editor, Taylor & Francis, Ltd., London, pp. 167–182, (1998).

Quere, L., et al., "Triterpenes as Potential Dimerization Inhibitors of HIV–1 Protease", *Biochemical and Biophysical Research Communications*, 227, pp. 484–488, (1996).

Recio, M.D., et al., "investigation on the Steroidal Anti–Inflammatory Activity of Triterpenoids from *Diospyros leucomelas*", *Planta Medica*, 61, pp. 9–12, (Feb. 1995).

Roberts, M.T., et al., "Birch (bark)", *Bookbinding and the Conservation of Books—A Dictionary of Descriptive Terminology* (Website), http://sul–server–2.standford.edu/don/dt/dt0328.html, 2 p., (Jun. 7, 2000).

Sanz, V., et al., "Synthesis of Ambrettolide from Phloionolic Acid", *Journal of the Chemical Society Perkin Transactions I*, (7), pp. 1837–1839, (Jul. 1982).

Schmidt, M.L., et al., "Betulinic acid induces apoptosis in human neuroblastoma cell lines", *European Journal of Cancer*, 33 (12), pp. 2007–2010, (Oct. 1997).

Schweizer, P., et al., "Induction of resistance in barley aagainst *Erysiphe graminis* f.sp. hordei by free cutin monomers", *Physiological and Molecular Plant Pathology*, 49, pp. 103–120, (1996).

Seoane, E., et al., "Total Synthesis and Stereochemistry of Phloionolic Acids", *Anales De Quimica*, 73, pp. 1336–1339, (1977).

Soler, F., et al., "Betulinic acid derivatives: a new class of specific inhibitors of human immunodeficiency virus type 1 entry", *Journal of Medicinal Chemistry*, 39 (5), pp. 1069–1083, (Mar. 1, 1996).

Taylor, L.T., "Properties of Supercritical Fluids", *Supercritical Fluid Extraction, Chapter 2*, John Wiley & Sons, New York, pp. 7–27, (1996).

Vilegas, J.H., et al., "Extraction of Low–polarity Compounds with Emphasis on Coumarin and Kaurenoic Acid from *Mikania glomerata* (Guaco) Leaves", *Phytochem. Anal.*, 8, Abstract Obtained from CAPLUS, Document No. 127:316461, 266–270, (1997).

Vilegs, J.H., et al., "Extraction of Low–polirity compuounds (with emphasis on coumarin and kaurenoic acid) from *Mikania glomerata* ('guaco') leaves", *Phytochemical Analysis*, vol. 8, No. 5, Accession No. PREV199799805753 XP002163896, 266–27i0, (1997).

Wang, J., et al., "Antibechic and expectorant constituents of Huashupi (*Betulae cortex*)", *Zhongguo Yaoxue Zazhi*, 29 (5), pp. 268–271, (1994).

Yasukawa, K., et al., "Sterol and triterpene derivatives from plants inhibit the effects of a tumor promoter, and sitsterol and betulinic acid inhibit tumor formation in mouse skin two–stage carcinogenesis", *Oncology*, 48 (1), pp. 72–76, (1991).

Seaone, E., "Synthesis of Ambrettolide from Phloionolic Acid", *Journal of Chem. Soc. Perkin Trans.*, (1982), 1837–1839.

\* cited by examiner

BIRCH BARK PROCESSING AND THE ISOLATION OF NATURAL PRODUCTS FROM BIRCH BARK

CROSS REFERENCE TO RELATED APPLICATION(S)

This application is a division of U.S. patent application Ser. No. 09/371,298, filed on Aug. 10, 1999, the specification of which is incorporated herein by reference.

BACKGROUND OF THE INVENTION

Birch bark is a low-value waste product in the forest industry today. Ekman, R., Holzforschung, (1983) 37, 205. Approximately 230,000 tons of birch bark are generated per year. For example, a single paper mill can generate 70 tons of birch bark per day. Thus, vast quantities of birch bark and its chemical components are available.

Birch bark is a potential source of a variety of organic chemicals. Several triterpenoids have been identified in birch bark extracts. For example, lupeol, betulin, betulinic aldehyde, betulinic acid, methyl betulinate, lupenone, betulonic aldehyde, betulonic acid, β-amyrin, erythrodiol, oleanolic aldehyde, oleanolic acid, methyl leanolate and acetyl oleanolic acid are all present in the outer bark of Betula verrucosa. Eckerman, C., (1985) Paperi ja Puu, No. 3, 100. In addition, several suberinic acids isolated from birch bark, as well as several triterpenoids, have been identified in the bark of Betula verrucosa. Ekman, R., Holzforschung, (1983) 37, 205.

The chemical constituents of birch bark are useful in pharmaceutical and industrial applications. For example, U.S. Pat. No. 5,750,578 discloses that betulin possesses antiviral properties and is useful to treat herpesvirus. Betulin also possesses antifeedant activity against boll weevils, and anti-inflammatory activity (Miles, D. H., 1994, J. Agric. Food. Chem., 42, 1561–1562 and Recio, M., Planta Med., 1995, 61, 9–12. In addition, betulin showed cough suppressant and expectorant effects. Jinuhua, W., Zhongguo Yaoxue Zazhi, (1994), 29(5), 268–71. Betulin is also a useful starting material for preparing alobetulin and derivatives thereof, which posses useful pharmacological properties.

Betulin can be converted to betulinic acid, which is useful as a therapeutic agent. For example, Pisha, E. et al., (1995) J. M. Nature Medicine, 1, 1046–1051 discloses that betulinic acid has antitumor activity against human melanoma, e.g., MEL-1, MEL-2 and MEL-4. In addition, Fujioka, T. et al., J. Nat. Prod., (1994) 57, 243–247 discloses that betulinic acid has anti-HIV activity in H9 lymphocytic cells.

Ambrettolide (cis-hexadec-7-enolide), a naturally occurring compound, is used to induce musk fragrance in perfumes. Ambrettolide is found in the vegetable oil of ambrette seeds. The synthesis of ambrettolide is accomplished from 9,10,18-trihydroxyoctadecanoic acid via a high-yielding multi-step synthesis. Seoane, E., J. Chem. Soc. Perkin Trans. (1982), 1837–1839. Therefore, 9,10,18-trihydroxyoctadecanoic acid, which is present in birch bark, is a useful precursor for the synthesis of ambrettolide.

9,10-Epoxy-18-hydroxyoctadecanoic acid is also present in birch bark. 9,10-Epoxy-18-hydroxyoctadecanoic acid is an environmentally-friendly spoilage deterrent and a rot-resistant additive for wood composites. Sweitzer, P., et al., Induction of Resistance in Barley Against Erysiphe graminis by Free Cutin Monomers, Physiol. Mol. Plant Pathol, (1996) 49(2) 103–120.

Suberin is another major component of birch bark. Suberin is an insoluble polymeric material that is attached to the cell walls of periderms. Kola, P.E. et al., Ann. Rev. Plant. Physiol., (1981), 32: 539–67. Suberin is generally an ester of fatty acids and polyphenolic polymers. Suberin of birch bark is typically a biopolyester of primary hydroxy, epoxy and dicarboxylic acids. Ekman, Holzforschung, (1983) 37, 205–211.

Suberin posseses several industrial applications. See, e.g., Taylor and Francis, Forests Products Biotechnology, A. Bruce and J. W. Palfreyman (editors), 167, 179–181 (1998); Peter E. Laks and Peggy A. McKaig, Flavonoid Biocides: Wood Preservatives Based on Condensed Tannins, Horzforschung, 42, 299–306 (1988); Etherington & Roberts, Dictionary—birch(bark), http://sul-server-2.stanford.edu/don/dt/dt0328.html, 1, Jun. 23, 1999; P. E. Kolattukudy, Structure, Biosynthesis, and Biodegradation of Cutin and Suberin, Ann. Rev. Plant Physiol., 32, 539–67 (1981); and N. Cordeiro, M. N. Belgasem, A. J. D. Silvestre, C. Pascol Neto, A. Gandini, Cork Suberin as a new source of chemicals, Int. Journal of Biological Materials, 22, 71080 (1998). Suberin is useful as a dispersant in many industrial applications (e.g., carbon black slurries, clay products, dyes, cement, oil drilling muds, and asphalt emulsifiers). Suberin is also useful in binders for animal pellets, conditioners for boiling water, anti-oxidants and additives to lead-storage battery plate expanders. McGraw-Hill Concise Encyclopedia of Science & Technology, Fourth Edition, 1998.

Polyphenolic polymers are also present in birch bark as a constituent of suberin. Polyphenolic polymers may be classified as soluble polyphenolic polymers or non-soluble polyphenolic polymers. Soluble polyphenolic polymers are the portion of polymers which are soluble in water under both acidic and basic conditions. The non-soluble polyphenolic polymers are non-soluble in water at a pH below about 4.0, but soluble in acetone, alcohols and other polar solvents. The non-soluble polyphenolic polymers may have a different formulation from the soluble polyphenolic polymers. However, the non-soluble polyphenolic polymers may be used in the same industrial applications as the soluble polyphenolic polymers.

Polyphenolic polymers are non-toxic and biodegradable and may be formulated for numerous purposes (e.g., as anti-oxidant reagents, anti-fingal materials, coating materials, co-polymers, wood preservatives, tire cord adhesives, foundry cord binders, rigid and floral foams, ion exchange resins, industrial water purification flocculants, textile dyes, food additives and pharmaceuticals). Pizzi, Wood Bark Extracts as Adhesives and Preservatives, 167–181, Taylor & Frances, Forest Products Biotechnology, Bruce and Palfreyman (editors), 1998.

Current methods for isolating the chemical constituents of birch bark are deficient in several ways. For example, betulin has been extracted from the bark of white-barked birches in amounts up to 30%, based on the dry weight of the bark. Elkman, R., (1983) Holzforsch, 37, 205; Ohara, S., et al., (1986) Mokuza Gakkaishi, 32, 266. In addition, Betulin has been isolated from outer birch bark waste of Betula verrucosa by liquid extraction employing boiling organic solvents and subsequent recrystallization. Eckerman, C., (1985) Paperi ja Puu, No. 3, 100. While current processes afford acceptable yields of betulin (e.g., 11–30%), these processes suffer from several major drawbacks. For example, the use of a boiling organic solvent, at standard pressure, in the extraction of betulin may destroy other useful compounds present in the bark. A need therefore exists for a method that can be used to extract betulin without damaging other compounds remaining in the birch bark.

Another drawback with the current extraction processes is that the organic solvents employed are hazardous, difficult to handle or difficult to dispose of. The typical organic solvents, which include methylene chloride and chloroform, are hazardous to humans (i.e., they are toxic or carcinogenic) and are hazardous to the environment. Considering the industrial scale on which the extraction processes would need to be performed in order to provide industrial quantities (e.g., tons) of betulin, large quantities of organic solvents would be required. The high cost of disposing the organic solvents is an additional disadvantage of the current extraction procedures.

Several methods have been devised for isolating polyphenolic polymers from birch trees. Some isolation methods are based on acid treatments in which the carbohydrate components (cellulose and hemicelluloses) are hydrolyzed to water-soluble materials. However, with such procedures, serious doubts exist as to whether the isolated polyphenolic polymer is representative of the "native" polyphenolic polymer. In addition, extraction conditions can cause undesirable rearrangements and other transformations of the polyphenolic structure that lead to a loss of useful properties. It is therefore desirable to have polyphenolic polymers in a form in which it is readily accessible, without involving costly, lengthy or dangerous procedures.

Suberin from *betula verucosa* contains at least 35 fatty acids which makes it hardly usable in industry. U.S. Pat. No. 4,732,708 issued to Ekman, R. et al. discloses a process for manufacturing suberinic acid. The process, however, does not attempt to separate the individual fatty acids. In addition, due to the crucial differences in the fundamental chemistry between the types of birch trees (i.e., the type and distribution of fatty acids), the procedures employed in U.S. Pat. No. 4,732,708 issued to Ekman, R. et al. may not be useful for the isolation of fatty acids from species of birch bark other than those employed in U.S. Pat. No. 4,732,708. As such, a method for isolating the individual fatty acids from the bark of other species of birch is needed.

The current methods employed to isolate not only betulin, but other components in birch bark (e.g., lupeol; betulinic acid; 9,10-epoxy-18-hydroxyoctadecanoic acid; 9,10,18-trihydroxyoctadecanoic acid; and polyphenolic polymers) are costly, inefficient or unsafe. A need therefore exists for safer, more cost-efficient methods to obtain commercial quantities (e.g., tons) of betulin; as well as commercial quantities (e.g., kg) of lupeol; betulinic acid; 9,10-epoxy-18-hydroxyoctadecanoic acid; 9,10,18-trihydioxyoctadecanoic acid; and polyphenolic polymers from birch bark. In addition, a need also exists for an industrial scale process for producing these products.

SUMMARY OF THE INVENTION

The present invention provides methods for isolating the chemical constituents of birch bark. Specifically, the present invention provides a method that can be used to extract betulin from birch bark without damaging other compounds remaining in the birch bark. In addition, the extraction processes employ solvents that are safe (non-toxic and non-carcinogenic), easy to handle, environmentally-friendly, inexpensive, and easy to dispose of. The present invention also provides a method for isolating polyphenolic polymers from birch trees wherein the polyphenolic polymers are in a form that is readily accessible and the methods do not involve costly, lengthy or dangerous procedures. The present invention also provides a method for isolating the individual fatty acids from the bark of various species of birch. The present invention also provides methods to provide commercial quantities (e.g., tons) of betulin; as well as commercial quantities (e.g., kg) of lupeol; betulinic acid; 9,10-epoxy-18-hydroxyoctadecanoic acid; 9,10,18-trihydroxyoctadecanoic acid; and polyphenolic polymers from birch bark.

The present invention provides a process for separating outer birch bark from inner birch bark comprising subjecting birch bark to fragmentation to provide a combination of outer birch bark shreds and inner birch bark chunks and separating the outer birch bark shreds from the inner birch bark chunks.

The present invention also provides a process that provides one or more (e.g., 1, 2, 3, or 4) natural products from outer birch bark. Accordingly, there is provided a process for obtaining one or more natural products from outer birch bark comprising subjecting the outer birch bark to supercritical fluid extraction to provide the natural product.

The present invention also provides a process for obtaining lupeol, betulinic acid and betulin from outer birch bark comprising extracting outer birch bark with carbon dioxide at a pressure between about 3,000 psi and 10,000 psi and at a temperature between about 50° C. and 100° C. to provide lupeol, betulin and betulinic acid.

The present invention also provides a process for obtaining lupeol, betulinic acid and betulin from outer birch bark using fractional supercritical fluid extraction comprising extracting with carbon dioxide at a pressure below about 5,000 psi and at a temperature below about 50° C. to provide a product comprising lupeol and extracting with carbon dioxide at a pressure of about 5,000 psi to about 10,000 psi and at a temperature of about 50° C. to about 120° C. to provide a product comprising a mixture of betulin and betulinic acid.

The present invention also provides a process for obtaining lupeol from outer birch bark comprising subjecting the outer birch bark to supercritical fluid extraction with carbon dioxide at a temperature of about 40° C. to about 50° C. and a pressure of about 3,000 psi to about 5,000 psi for a period of time of about 1 hour to about 3 hours to provide the lupeol.

The present invention also provides a process for obtaining betulin and betulinic acid from outer birch bark comprising subjecting the outer birch bark to supercritical fluid extraction with carbon dioxide at a temperature of about 80° C. to about 100° C. and a pressure of about 8,000 psi to about 10,000 psi for a period of time of about 3 hours to about 5 hours to provide a mixture of betulin and betulinic acid.

The present invention also provides a process for isolating 9,10-epoxy-18-hydroxyoctadecanoic acid from outer birch bark comprising: (1) subjecting the outer birch bark to alkali hydrolysis in an aqueous alcohol solution to provide a second outer birch bark and a second solution; (2) separating the second solution from the second outer birch bark; (3) condensing the second solution at a temperature below about 50° C. to form a third solution; (4) adding water to the third solution to form a precipitate and a fourth solution; (5) separating the precipitate from the fourth solution; (6) acidifying the fourth solution to a pH of about 5.5 to about 6.5 to give a fifth solution and 9,10-epoxy-18-hydroxydecanoic acid as a precipitate; and (7) separating the 9,10-epoxy-18-hydroxydecanoic acid precipitate from the fifth solution to give 9,10-epoxy-1 8-hydroxydecanoic acid.

The present invention also provides a process for isolating 9,10,18-trihydroxyoctadecanoic acid from outer birch bark comprising: (1) subjecting the outer birch bark to alkali hydrolysis in an aqueous alcohol solution to provide a second outer birch bark and a second solution; (2) separating the second solution from the second outer birch bark; (3) condensing the second solution at a temperature below about 50° C. to form a third solution; (4) adding water to the third solution to form a first precipitate and a fourth solution; (5) separating the first precipitate from the fourth solution; (6) acidifying the fourth solution to a pH of about 5.5 to about 6.5 to give a fifth solution and a second precipitate; (7) separating the second precipitate from the fifth solution; (8) condensing the fifth solution to provide a sixth solution; (9) subjecting the sixth solution to epoxidizing conditions to provide an epoxide and hydrolyzing the epoxide to provide a seventh solution; and (10) crystallizing the seventh solution to give 9,10,18-trihydroxyoctadecanoic acid.

The present invention also provides a process for isolating non-soluble polyphenolic polymers and fatty acids from outer birch bark comprising: (1) subjecting the outer birch bark to alkali hydrolysis in an aqueous alcohol solution to provide a second birch bark and a second solution; (2) separating the second solution from the second outer birch bark; (3) adding water to the second outer birch bark to provide a third solution and a third outer birch bark; (4) separating the third solution from the third outer birch bark; (5) acidifying the third solution to a pH of about 3.0 to about 4.0 to give a fourth solution and a mixture of non-soluble polyphenolic polymer and fatty acids; and (6) separating the mixture of fatty acids and non-soluble polyphenolic polymers from the fourth solution.

The present invention also provides a process for isolating fatty acids and soluble polyphenolic polymers from outer birch bark comprising: (1) subjecting the outer birch bark to alkali hydrolysis in an aqueous alcohol solution to provide a second outer birch bark and a second solution; (2) separating the second solution from the second outer birch bark; (3) adding water to the second outer birch bark to provide a third outer birch bark and a third solution; (4) separating the third solution from the third outer birch bark; (5) acidifying the third solution to a pH of about 3.0–4.0 to give a fourth solution and a solid; (6) separating the solid from the fourth solution; (7) adding an alcohol to the fourth solution to provide a fifth solution and a precipitate; (8) separating the precipitate from the fifth solution; and (9) condensing the fifth solution to provide a mixture of fatty acids and soluble polyphenolic polymers.

DETAILED DESCRIPTION OF THE INVENTION

Specific values listed below for ranges are for illustration only; they do not exclude other defined values or other values within defined ranges.

Separation of Inner Birch Bark from Outer Birch Bark:

As used herein, "birch" is any of the several deciduous trees of the genus Betula. The birches comprise the family Betulaceae in the order Fagales. Birch trees include, for example, white birch, *B. alba*; sweet, black or cherry birch, *B. lenta*; monarch birch, *B. Maximowicziana*; dwarf or arctic birch, *B. Nana*; Japanese white birch, *B. Platyphyla Japonica*; smooth-bark birch, *B. Pubescens*; yellow birch, *B. alleghaniensis*; paper, white or canoe birch, *B. papyrifera*; grey birch, *B. populifolia*; river birch, *B. nigra*; and the European birches, *B. pubescens; B. Alba* and *B. pendula*. Specifically, birch can be *B. alba, B. lenta, B. Maximowicziana, B. Nana, B. Platyphyla Japonica, B. Pubescens, B. alleghaniensis, B. papyrifera, B. populifolia, B. nigra, B. pubescens, B. Alba* or *B. pendula*. A specific birch for use in the processes of the present invention is *B. papyrifera*.

As used herein, "fragmentation" includes chopping, crunching, crushing, gnashing or pounding. Such fragmentation of birch bark will effectively provide inner birch bark (e.g., in the form of chunks) and outer birch bark (e.g., in the form of shreds) which can be physically separated. The fragmentation can conveniently be carried out by feeding birch bark into a machine with knives on a rotating disk (e.g., a chipper or shredder). One chipper suitable for fragmenting the bark is the YardMan Model 246-648D401 chipper.

Figure 1A:
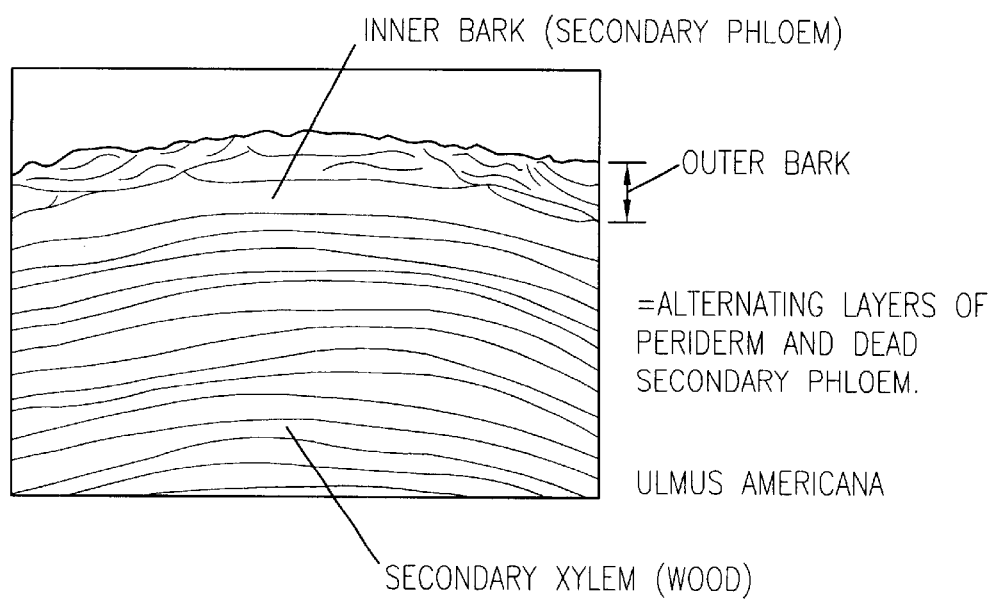
FIG. 1(a) illustrates outer and inner birch bark (cross-sectional view).
Figure 1B:
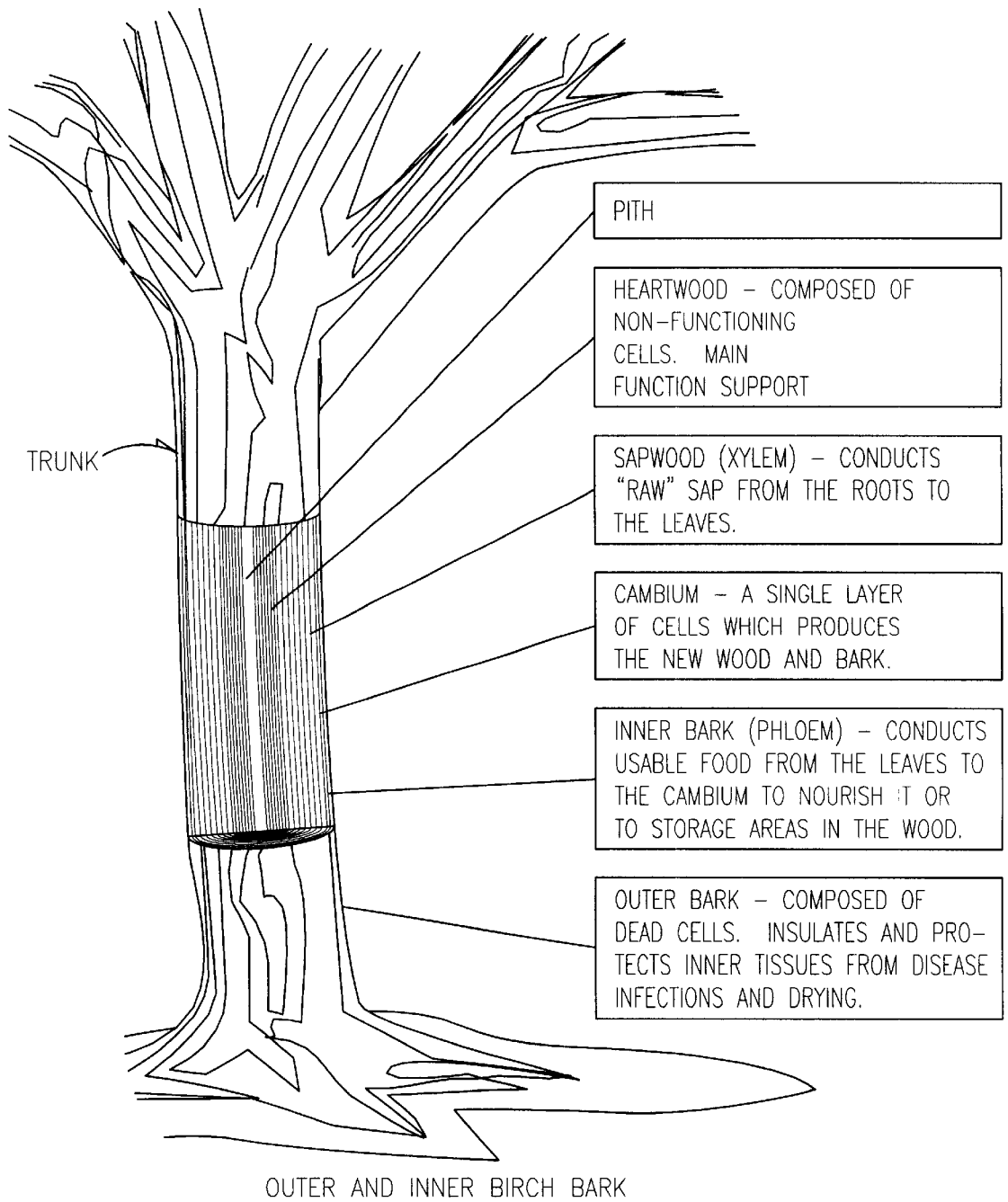
FIG. 1(b) illustrates outer and inner birch bark.

As illustrated in FIG. 1(a) and FIG. 1(b), birch bark consists of inner birch bark and outer birch bark. Inner birch bark is more dense and granular than outer birch bark, while outer birch bark is more flexible and fibrous than inner birch bark. In addition, outer birch bark is light in color, thin (1–5 mm), tough, and of low water-content relative to inner birch bark. The inner bark is darker in color, thicker (3–10 mm) and non-fibrous relative to the outer bark. The inner bark is the portion of the tree wherein significant water transport occurs (i.e., an area of high water content). Due to the differences in the physical properties of inner birch bark and outer birch bark, Applicant has found that fragmentation produces outer birch bark shreds and inner birch bark chunks.

Outer birch bark shreds can be separated from the inner birch bark chunks using any suitable means. The separation can conveniently be accomplished by screening the mixture through a mesh having openings intermediate in size between the smaller inner bark chunks and the larger outer bark shreds. The smaller inner bark chunks fall through the screen and are separated from the outer bark.

The "mesh" can be a unit comprising one or more open spaces in a cord, thread, or wire network in which the cords, threads or wires surround the spaces. Any mesh suitable to separate inner birch bark from outer birch bark can be employed. Typically, the mesh is a wire mesh containing openings of about ½ of an inch by ½ of an inch, or smaller.

For example, mesh can conveniently contain openings of about ¼ of an inch by about ¼ of an inch. Specifically, the size of the mesh can be about 20 mm by about 20 mm, or about 10 mm by about 10 mm, or about 6 mm by about 6 mm. More specifically, the size of the mesh can be about 3 mm by about 3 mm.

Figure 9:
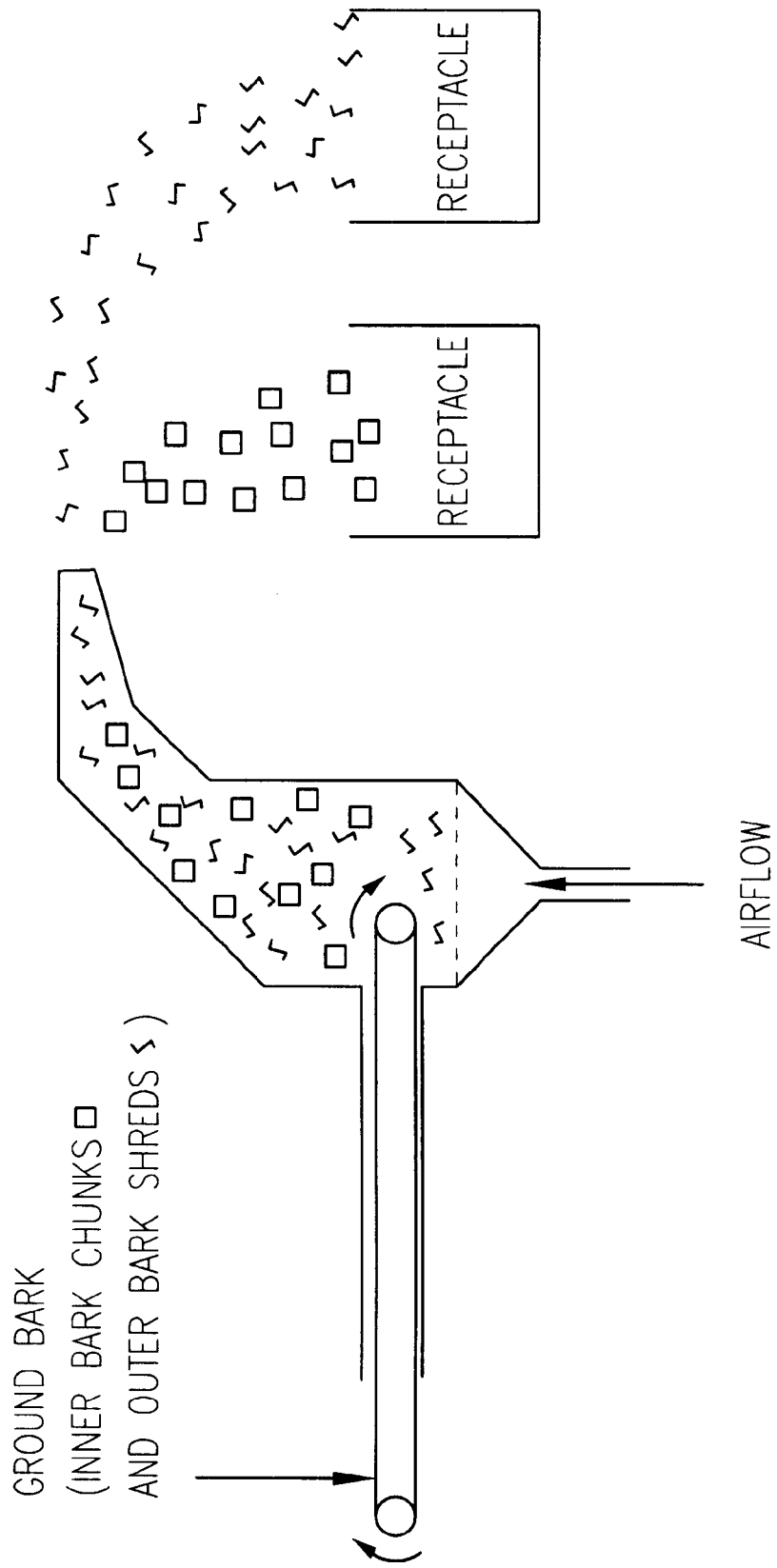
FIG. 9 illustrates the separation of outer and inner bark with an air classifier.

Alternatively, the inner birch bark chunks and outer birch bark shreds may be separated with the use of an air classifier as shown in FIG. 9. As used herein, an "air classifier" is a device which operates on the principle of the differing properties of the two components (e.g., inner and outer birch bark) in an air stream to effect a physical separation. Typically, the less dense outer bark travels a greater distance in the air stream than the more dense inner bark. The inner bark, along with other materials, falls rapidly from the stream of air. As a result, the inner birch bark and the outer birch bark can be separated.

After separating outer birch bark from inner birch bark, outer birch bark of about 10 wt. % to about 45 wt. % based on initial birch bark content is typically obtained and inner birch bark of about 55 wt. % to about 85 wt. % is typically obtained.

For use in the processes of the present invention, birch bark shreds less than about 10 mm in diameter can conveniently be used. More specifically, outer birch bark shreds less than about 6 mm in diameter, less than about 4 mm in diameter, or less than about 2 mm in diameter, can be used.

Figure 2:
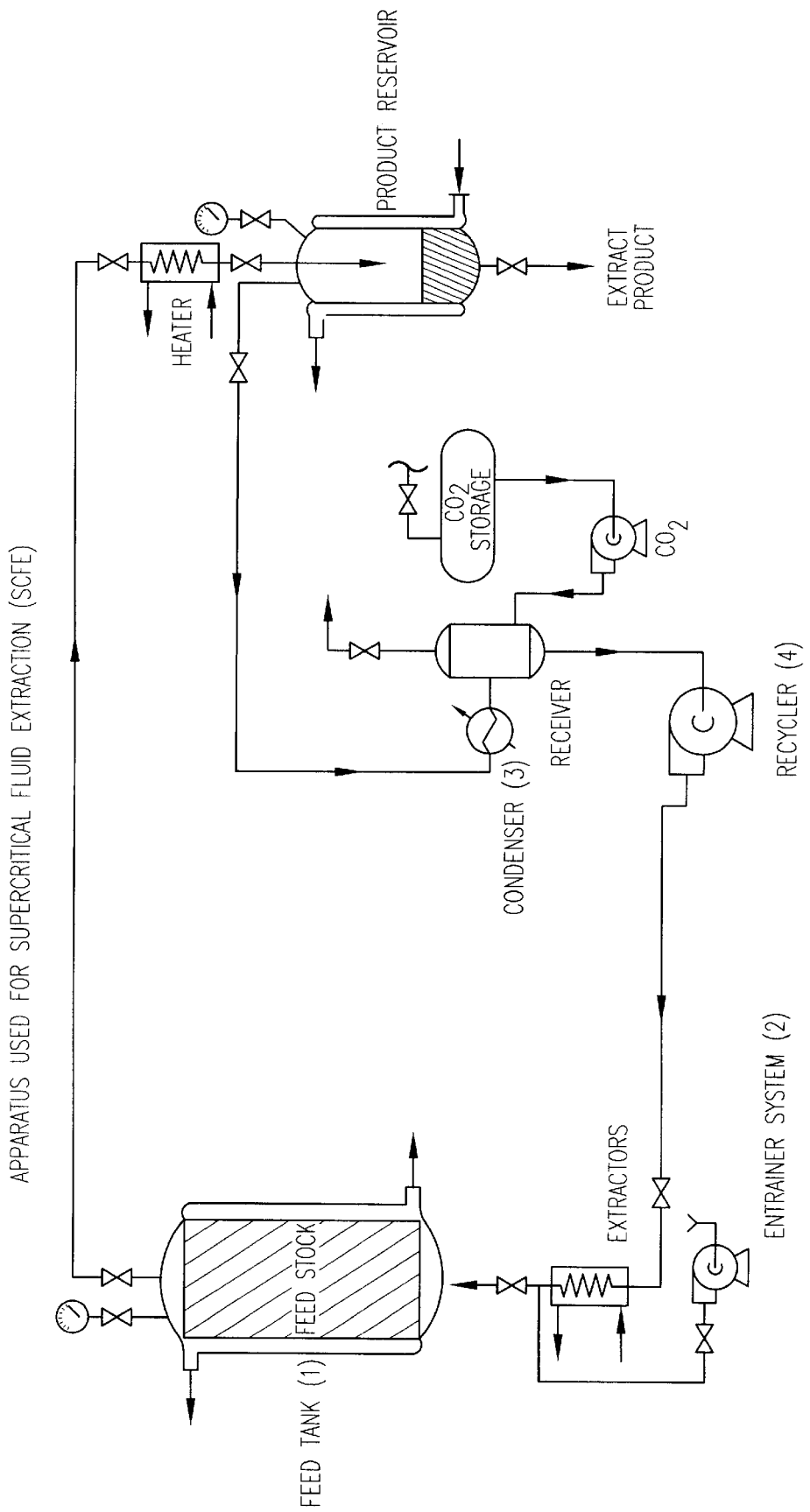
FIG. 2 illustrates an apparatus for supercritical fluid extraction.

Supercritical Fluid Extraction:

As illustrated in FIG. 2, a natural product (e.g., betulin, betulinic acid or lupeol) can be obtained from outer birch bark by supercritical fluid extraction. The outer birch bark is introduced into a feed tank (1) through the opened lid on the top. The birch bark is heated at an elevated pressure in a solvent comprising carbon dioxide. The solution is transferred to a product reservoir (2). Extracted product is removed and the solvent comprising carbon dioxide is passed though a condenser (3) and subsequently recycled into the feed tank (1) through a recycler (4).

As used herein, "natural product" is any of the compounds naturally occurring in the bark of birch. Natural products specifically include triterpenoids.

According to the biogenetic isoprene rule, a "triterpenoid" is a hydrocarbon, or its oxygenated analog, that is derived from squalene by a sequence of straightforward cyclizations, functionalizations, and sometimes rearrangement.

A specific triterpenoid present in birch bark is betulin (lup-20(29)-ene-3,28-diol), lupeol (lup-20(29)-en-3β-ol), or betulinic acid (lup-20(29)-en-3β-ol-28-oic acid).

The processes of the present invention provide natural products of birch bark. Each natural product may have one or more chiral centers and may exist in and be isolated in optically active and racemic forms. It is to be understood that the present invention provides processes for isolating natural products in any racemic, optically-active, polymorphic, or stereoisomeric form, present in the native bark or isolated after exposure to the processes of the invention. When a process of the invention provides a mixture of enantiomers or isomers, it is appreciated that those skilled in the art can separate optically active forms (for example, by resolution of the racemic form by recrystallization techniques or by chromatographic separation using a chiral stationary phase) if a single enantiomer is desired.

Supercritical fluid extraction is an extraction wherein a fluid at a temperature and pressure above its critical point is employed; or a fluid above its critical temperature, regardless of pressure, is employed. Below the critical point, the fluid can coexist in both gas and liquid phases, but above the critical point there is only one phase. Equipment and techniques for carrying out supercritical fluid extraction are known to those skilled in the art. See, McHugh, M. And Krukonis, V., *Supercritical Fluid Extraction*, 2nd ed, Butterworth-Heinemann, Boston, 1994; Johnston, K. P., Penninger, J. M. L., *Supercritical Fluid Science and Technology*, ACS Symposium Series 406, American Chemical Society, Washington, D.C.; and Taylor, L. T., *Supercritical Fluid Extraction*, John Wiley & Sons, New York, 1996.

In a supercritical fluid extraction, thermodynamic and transport properties of supercritical fluid are a function of density, which depends strongly on the fluid's pressure and temperature. The density may be adjusted from a gas-like value of 0.1 g/ml to a liquid-like value as high as 1.2 g/ml. Furthermore, as conditions approach the critical point, the effect of temperature and pressure on density becomes much more significant. For example, increasing the density of supercritical carbon dioxide from 0.2 to 0.5 g/ml requires raising the pressure from 85 atm to 140 atm (8.6 megapascals to 14.2 megapascals) at 158° F. (70° C.), but at 95° F. (35° C.) the required change is only from 65 atm to 80 atm (6.61 Mpa to 8.1 Mpa).

As used herein, "fractional supercritical fluid extraction" (hereinafter "FSCFE") is a multi-step procedure wherein the supercritical fluid extraction is carried out at one temperature and pressure for a given period of time and is then carried out at one or more other temperatures or pressures.

The efficiency of supercritical fluid extraction on a material such as outer birch bark depends in part upon the size of the outer birch bark pieces. Thus, the smaller the outer birch bark pieces, the more efficient the supercritical fluid extraction typically will be. As such, after fragmentation and prior to extraction, outer birch bark shreds may be further reduced in size with a Hammermill or suitable means. For example, a 15 horsepower 3B Junior Hammermill made by Jay Bee Manufacturing, Inc can be used as illustrated in the Examples herein below. The hammermill reduces large pieces of birch bark by beating the bark with pivoted hammers until the material is small enough to fall through a mesh.

For use in the processes of the present invention, the size of outer birch bark shreds obtained after the Hammermill reduction is typically less than about 5 mm in diameter. Specifically, the shreds can be less than about 3 mm in diameter. More specifically, the shreds can be less than about 1 mm in diameter.

Prior to fragmentation or extraction, outer birch bark may be dried of any water present. Such drying may increase the efficiency of the fragmentation. Birch bark may be air-dried or dried at an elevated temperature with or without reduced pressure (i.e., in vacuo). Specifically, birch bark may be dried in vacuo at an elevated temperature. Machines capable of drying bark are known in the art and include an oven, or similar device, such as a rotating air drum drier.

For use in the processes of the present invention, supercritical fluid extraction can conveniently be carried out at a pressure of about 1,000 psi to about 12,000 psi. It is appreciated that those skilled in the art understand that higher pressures may enable faster extraction. In this case, it may be necessary to subsequently separate and purify the product (e.g., lupeol, betulin, betulinic acids, other minor triterpene or acidic admixtures).

For use in the processes of the present invention, supercritical fluid extraction can conveniently be carried out at a pressure of about 750 psi to about 12,000 psi. Specifically, the pressure may be about 1,000 psi to about 10,000 psi.

More specifically, the pressure may be about 4,000 psi to about 9,000 psi.

For use in the processes of the present invention, the temperature at which the birch bark may be dried is greater than about 30° C. Specifically, the temperature is greater than about 45° C. More specifically, the temperature is greater than about 60° C.

For use in the processes of the present invention, the temperature of supercritical fluid extraction can conveniently be about 0° C. to about 150° C. Specifically, the temperature can be about 25° C. to about 110° C. More specifically, the temperature can be about 45° C. to about 100° C.

In one specific embodiment, supercritical fluid extraction is performed at a temperature of about 40° C. to about 90° C. and a pressure of about 3,000 psi to about 10,000 psi.

Supercritical fluid extraction employs a solvent which possesses physical properties suitable as a supercritical fluid. Suitable solvents include carbon dioxide, Xe, Freon-23, ethane, $N_2O$, $SF_6$, propane, ammonia, n-$C_4H_{10}$, $(C_2H_5)_2O$ and the like.

The physical properties of carbon dioxide make it particularly attractive as a solvent for supercritical fluid extraction. Carbon dioxide is a major component of the atmosphere and is therefore relatively safe and abundant. In addition, carbon dioxide is relatively inexpensive. Compared to most other suitable solvents, carbon dioxide is environmentally friendly as it will not harm the atmosphere at the quantities used in the methods of the invention. Moreover, carbon dioxide is non-flammable and non-explosive. Further, carbon dioxide leaves no substantial residue or remnant upon evaporation.

Carbon dioxide also possesses physical properties which enable it to change polarity over the temperature range and pressure range normally employed in supercritical fluid extraction. As a result, carbon dioxide may act as a nonpolar solvent at one temperature and pressure but may act as a polar solvent at another temperature and pressure. By varying the temperature and pressure, the solvent properties may be modified. This allows for the isolation of more than one compound using a single solvent system.

The solvent employed in supercritical fluid extraction may be a single compound or may be a mixture of compounds. In addition, the solvent may include an additive.

As used herein, an "additive" is a compound added to the solvent in an amount of about 1 wt % to about 20 wt. % based on the solvent. Specifically, the additive may be present in an amount of about 1 wt. % to about 15 wt. % or about 1 wt. % to about 10 wt. %. Upon addition, the additive will modify the physical properties of the solvent. For example, an additive may be useful to modify the polarity, critical temperature, critical pressure, etc., of the solvent system.

Suitable additives include lower alcohols (e.g., methanol, ethanol, 1-propanol, 2-propanol, 1-hexanol, or 2-methoxy ethanol); ethers (e.g., tetrahydrofuran or 1,4-dioxane); substituted hydrocarbons (e.g., acetonitrile, dichloromethane, ammonia or chloroform) propylene carbonate, N,N-dimethylaceamide; dimethyl sulfoxide; carboxylic acids (e.g., formic acid); water; carbon disulfide; lower ketones (e.g., acetone), hydrocarbons (e.g., propane, toluene, hexanes and pentanes).

Applicant has found that utilizing a solvent comprising carbon dioxide in supercritical fluid extraction, lupeol is soluble at a temperature below about 50° C. and a pressure below about 5,000 psi. In addition, Applicant has found that following removal of lupeol, betulin and betulinic acid can be extracted using a solvent comprising carbon dioxide at a temperature of about 50° C. to about 120° C. and a pressure of about 5,000 psi to about 10,000 psi.

Accordingly, the processes of the invention can conveniently include a fractional supercritical fluid extraction of outer birch bark employing a solvent comprising carbon dioxide at a pressure below about 5,000 psi at a temperature below about 50° C. to provide lupeol followed by an extraction employing a solvent comprising carbon dioxide at a pressure of about 5,000 psi to about 10,000 psi and at a temperature of about 50° C. to about 120° C. to provide betulin and betulinic acid.

The processes of the invention can conveniently include a fractional supercritical fluid extraction comprising extracting outer birch bark with a solvent comprising carbon dioxide for a period of time greater than about 30 minutes at a pressure below about 5,000 psi and at a temperature below about 50° C. to provide lupeol followed by extracting with a solvent comprising carbon dioxide for a period of time greater than about 30 minutes at a pressure of about 5,000 psi to about 10,000 psi and at a temperature of about 50° C. to about 120° C. to provide a mixture of betulin and betulinic acid.

The processes of the invention can conveniently include a fractional supercritical fluid extraction comprising extracting with a solvent comprising carbon dioxide for a period of time of about 1 hour to about 3 hours at a pressure of about 3,000 psi to about 5,000 psi and at a temperature of about 40° C. to about 50° C. to provide lupeol and betulin followed by extracting with a solvent comprising carbon dioxide for a period of time of about 3 hours to about 5 hours at a pressure of about 8,000 psi to about 10,000 psi and at a temperature of about 80° C. to about 100° C. to provide a mixture of betulin and betulinic acid.

The processes of the invention can also include non-fractional supercritical fluid extraction comprising extracting with a solvent comprising carbon dioxide. The extraction can conveniently be carried out for a period of time of about 3 hours to about 5 hours at a pressure of about 5,000 psi to about 10,000 psi and at a temperature of about 80° C. to about 100° to provide a mixture of lupeol, betulin and betulinic acid.

Betulin

The betulin from the mixture of lupeol, betulin and/or betulinic acid obtained from supercritical fluid extraction may be purified using techniques that are known in the art for purification of natural products, e.g., by recrystallization or by chromatography. Suitable solvents for crystallization of betulin include, for example, an alcohol (e.g., isopropanol). After purification, betulin is typically at least 90% pure. Specifically, betulin is at least 95% pure, or at least 97% pure.

Typically, the processes of the present invention provide betulin in a yield of about 10 wt % to about 25 wt. % based on outer birch bark. Specifically, the yield is about 15 wt % to about 20 wt. % based on outer birch bark, or about 17 wt % to about 20 wt. % based on outer birch bark.

Using the procedures of the present invention, betulin can be recovered in about 15 wt. % to about 25 wt. %, based on birch bark. This represents as much as a 25% improvement over other methods for betulin isolation. O'Connell, M. M.; Bentley, M. D.; Campbell, C. S.; Cole, B. J. W.; *Phytochemistry* (1988) 27, 2175–2176; Lugemwa, F. N.; Huang, F. Y.; Bentley, M. D.; Mendel, M. J.; Alford, A. R.; *J. Agric. Food Chem.*, (1990), 36, 493–496.

Betulinic Acid

Betulinic acid may be separated and purified through the specific formation of non-soluble aluminum salts of betulinic acid with aluminum alcoholates. As used herein, "alcoholate" is an organic alcohol wherein the hydroxy hydrogen has been replaced with a metal, e.g., $(CH_3CH_2O)_3Al$. Aluminum alcoholates are suitable reagents for triterpene purification because it is believed that aluminum alcoholates bind strongly and irreversibly to acids and tannins, therefore providing complete discoloration of the total extract.

A suitable aluminum alcoholate is aluminum isopropoxide, however, other alcoholates, basic materials or ion exchange resins may be employed to purify the betulinic acid.

Further purification of betulinic acid from aluminum salts may be provided using techniques that are known in the art for the purification or isolation of natural products, e.g., by washing with solvent, crystallization, using ion exchange resins, through the formation of esters or by chromatography. After purification, betulinic acid is typically at least 90% pure. Specifically, betulinic acid is at least 95% pure, or at least 99% pure.

The processes of the present invention yield betulinic acid, after purification, that is about 0.5 wt. % to about 2 wt. % based on outer birch bark. Specifically, betulinic acid is about 1 wt. % to about 1.5 wt. % based on outer birch bark, or about 0.5 wt. % to about 1 wt. % based on outer birch bark.

Although betulinic acid is reported as being present in birch bark, the isolation, separation and purification of betulinic acid from birch bark has not been previously reported. The processes of the present invention yield betulinic acid of about 0.5 wt. % to 2 wt. % based on the outer bark of *betula paparifera*. In addition, the processes of the present invention may be used to isolate betulinic acid present in other kinds of birch bark. Moreover, the processes of the present invention (e.g., SCFE) may be used to separate and isolate betulinic acid from other kinds of plant extracts.

Lupeol

The processes of the present invention yield lupeol, after purification, that is about 0.5 wt % to about 2 wt. % based on outer birch bark. Specifically, the lupeol is about 1 wt% to about 1.5 wt. % based on outer birch bark, or about 0.5 wt % to about 1.0 wt. % based on outer birch bark.

The lupeol obtained from the supercritical fluid extraction may also be purified using techniques that are known in the art for purification of natural products, e.g., by recrystallization or by chromatography on silica gel or other suitable supports. Suitable solvents for chromatographic purification of lupeol include, for example, a non-polar solvent (e.g., hexanes:ether, 4:1). After purification, lupeol is typically at least 90% pure. Specifically, lupeol is at least 95% pure, or at least 98% pure.

Using the procedures of the present invention, lupeol can be recovered in about 0.5 wt. % to about 2 wt. %, based on birch bark. This represents as much as a 70% improvement over other methods for lupeol isolation. O'Connell, M. M.; Bentley, M. D.; Campbell, C. S.; Cole, B. J. W.; *Phytochemistry* (1988) 27, 2175–2176; Lugemwa, F. N.; Huang, F. Y.; Bentley, M. D.; Mendel, M. J.; Alford, A. R.; *J. Agric. Food Chem.*, (1990), 36, 493–496.

Applicant has discovered that betulin, lupeol and betulinic acid may be isolated from outer birch bark in good yield and purity, using supercritical fluid extraction. Conditions previously known for isolating one or more of these compounds damage much of the suberin present in the bark. SCFE, however, is a milder technique which does not destroy the oxirane rings of suberin.

Figure 4:
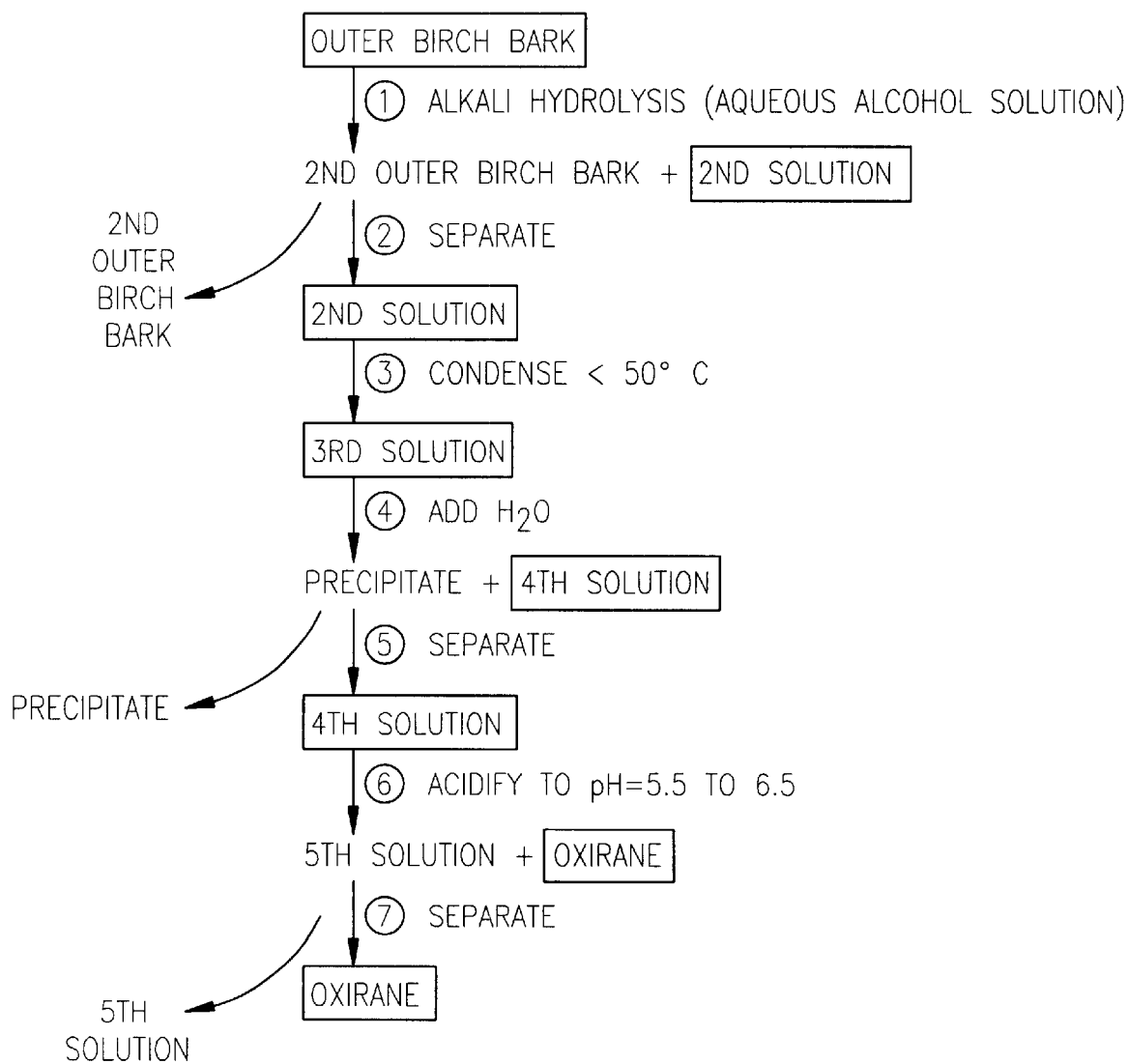
FIG. 4 is a schematic illustration of the isolation of 9,10-epoxy-18-hydroxyoctadecanoic acid from outer birch bark.

Isolation of 9,10-Epoxy-18-Hydroxydecanoic Acid (FIG. 4):

As illustrated in FIG. 4, step 1, outer birch bark is subject to alkali hydrolysis. As used herein, "alkali hydrolysis" includes any condition suitable for saponifying ester bonds. The reaction (i.e., alkali hydrolysis) can conveniently be carried out in an aqueous alcohol solution under basic catalysis.

As used herein, "alcohol" is a compound containing at least one C(OH) group. Particular alcohols for use in the present invention will have between about 1 and about 10 carbon atoms; may be cyclic or aliphatic; may be saturated or unsaturated; and may be branched or straight-chained. Specific alcohols suitable for use in the present invention include methanol, ethanol, iso-propanol, tert-butanol, 1-hepten-3-ol and 1-octen-3-ol.

As used herein, "aqueous alcohol solution" is a solution comprising water and an alcohol. Typically, the alcohol is present in at least 20, 50, or 75 wt. % of the solution. Specifically, the alcohol is present in about 90 wt. % of the solution or in about 95 wt. % of the solution. As illustrated in the Examples herein below, a specific aqueous alcohol solution suitable for use in the processes of the present invention is about 5% water in isopropanol.

Suitable bases include metal hydroxides and metal alkoxides. Suitable metal hydroxides include sodium hydroxide, potassium hydroxide, lithium hydroxide, calcium hydroxide and barium hydroxide. Suitable metal alkoxides include lithium methoxide, lithium ethoxide, lithium isopropoxide, lithium tertbutoxide, sodium methoxide, sodium ethoxide, sodium isopropoxide, sodium tertbutoxide, potassium methoxide, potassium ethoxide, potassium isopropoxide, potassium tert-butoxide, magnesium methoxide, magnesium ethoxide, barium methoxide, barium ethoxide, calcium methoxide and calcium ethoxide.

A specific base suitable for the processes of the present invention is sodium hydroxide.

Figure 3:
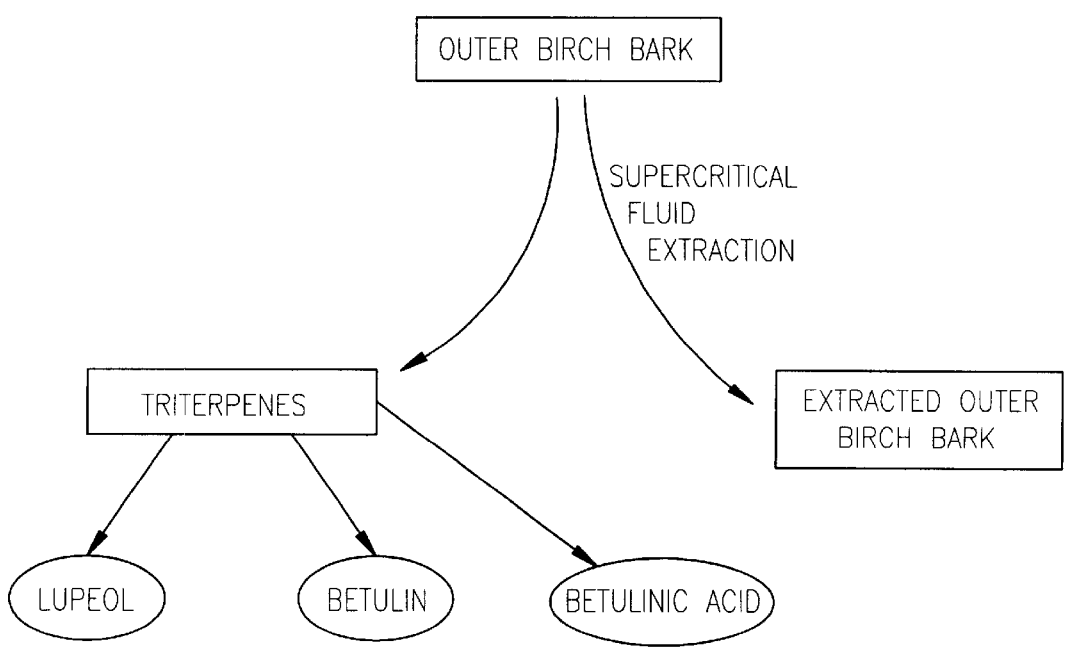
FIG. 3 is a schematic illustration of the isolation of lupeol, betulin and betulinic acid from outer birch bark.

Prior to alkali hydrolysis, outer birch bark can optionally be subject to extraction as illustrated in FIG. 2 and FIG. 3 to provide extracted outer birch bark. As used herein, "extraction" is the act of obtaining one or more compounds by chemical or mechanical action, as by pressure, distillation, or evaporation as described herein above. Extraction includes the use of a solvent, for example, water or an organic solvent, at standard temperature and pressure. In addition, extracting also includes supercritical fluid extraction.

Extracting outer birch bark is usefuil to remove compounds that may interfere with the subsequent hydrolysis, or that may contaminate the hydrolysis product. For example, lupeol and betulin are optionally removed from the outer birch bark prior to the outer birch bark being subject to alkali hydrolysis to facilitate the isolation of 9,10-epoxy-18-hydroxyoctadecanoic acid from outer birch bark.

As illustrated in FIG. 4, step 2, the second solution (i.e., aqueous alcohol solution) is separated from the second outer birch bark. The solution can be separated using any suitable technique for removing a solid from a liquid. For example, the separation can be accomplished by filtering, hot filtering, or centrifuging. Specifically, the second solution can be separated from the second outer bark by filtering, and more specifically, by hot filtering. "Hot filtering" includes filtering a solid from a liquid wherein both the solid and liquid, prior to filtering, are at a temperature above about 40° C. Specifically, the temperature is above about 55° C. More specifically, the temperature is above about 70° C.

As illustrated in FIG. 4, step 3, the second solution is condensed at a temperature below about 50° C. to provide a third solution. The solution can be condensed using any suitable technique that is known in the art. For example, "condensing" can include evaporating or evaporating in vacuo. Specifically, condensing can occur by evaporating in vacuo at a temperature less than about 50° C. or evaporating in vacuo at a temperature less than about 35° C. More specifically, condensing can occur by evaporating in vacuo at a temperature less than about 30° C. Condensing can conveniently be carried out for a period of time sufficient to reduce the volume of the solution at least about 20%, 50%, 75% or 90%.

Applicant has found that the temperature of condensing (e.g., evaporation) influences the ability to isolate 9,10-epoxy-18-hydroxyoctadecanoic acid from outer birch bark. Applicant has found that the temperature during condensing preferably should be kept below about 50° C. If the temperature during condensing is kept below about 50° C., 9,10-epoxy-18-hydroxyoctadecanoic acid will not readily decompose to 9,10,18-trihydroxyoctadecanoic acid, and a higher yield of 9,10-epoxy-18-hydroxyoctadecanoic acid can be obtained.

As illustrated in FIG. 4, step 4 and step 5, water, or another suitable solvent, is added to the third solution to form a precipitate and a fourth solution, and the precipitate is separated from the fourth solution. The precipitate can be separated using any suitable technique known in the art. For example, it may be separated by filtering, hot filtering, or centrifuging. However, the precipitate typically has a clay-like form. As such, filtration of the precipitate can be extremely difficult. However, the precipitate can conveniently be separated from the fourth solution by centrifuging.

As illustrated in FIG. 4, step 6, the fourth solution is acidified to a pH of about 5.5 to about 6.5 to give a fifth solution and 9,10-epoxy-18-hydroxydecanoic acid (i.e., oxirane) as a precipitate. The pH of the fourth solution may be lowered by the addition of a suitable acid. Suitable acids include, for example, hydrochloric acid, phosphoric acid, formic acid, hydrobromic acid, sulfuric acid, nitric acid, acetic acid, and the like.

Typically, the pH should be lowered to a value from about 5.5 to about 6.5. If the pH is kept between 5.5 and 6.5, the 9,10-epoxy-18-hydroxyoctadecanoic acid will not readily decompose to 9,10,18-trihydroxyoctadecanoic acid. In addition, the yield of 9,10-epoxy-18-hydroxyoctadecanoic acid decreases if the pH is not carefully controlled. For example, if the pH falls below 4.0, the 9,10-epoxy-18-hydroxyoctadecanoic acid is hydrolyzed to the corresponding diol in less than two hours at room temperature.

As illustrated in FIG. 4, Step 7, the 9,10-epoxy-18-hydroxyoctadecanoic acid precipitate (i.e., oxirane) is separated from the fifth solution. The the oxirane can be separated from the fifth solution using any suitable technique. For example, the oxirane can be separated by filtering, hot filtering, or centrifuging. Specifically, the oxirane can be separated by filtering, as illustrated in the Examples herein below.

The oxirane can optionally be purified using any suitable technique known in the art. For example, the oxirane can be purified by recrystallization, extraction, chromatography or sublimation. Specifically, the oxirane can be purified by recrystallization from an alcohol (e.g., isopropanol), as illustrated in the Examples herein below.

Figure 5:
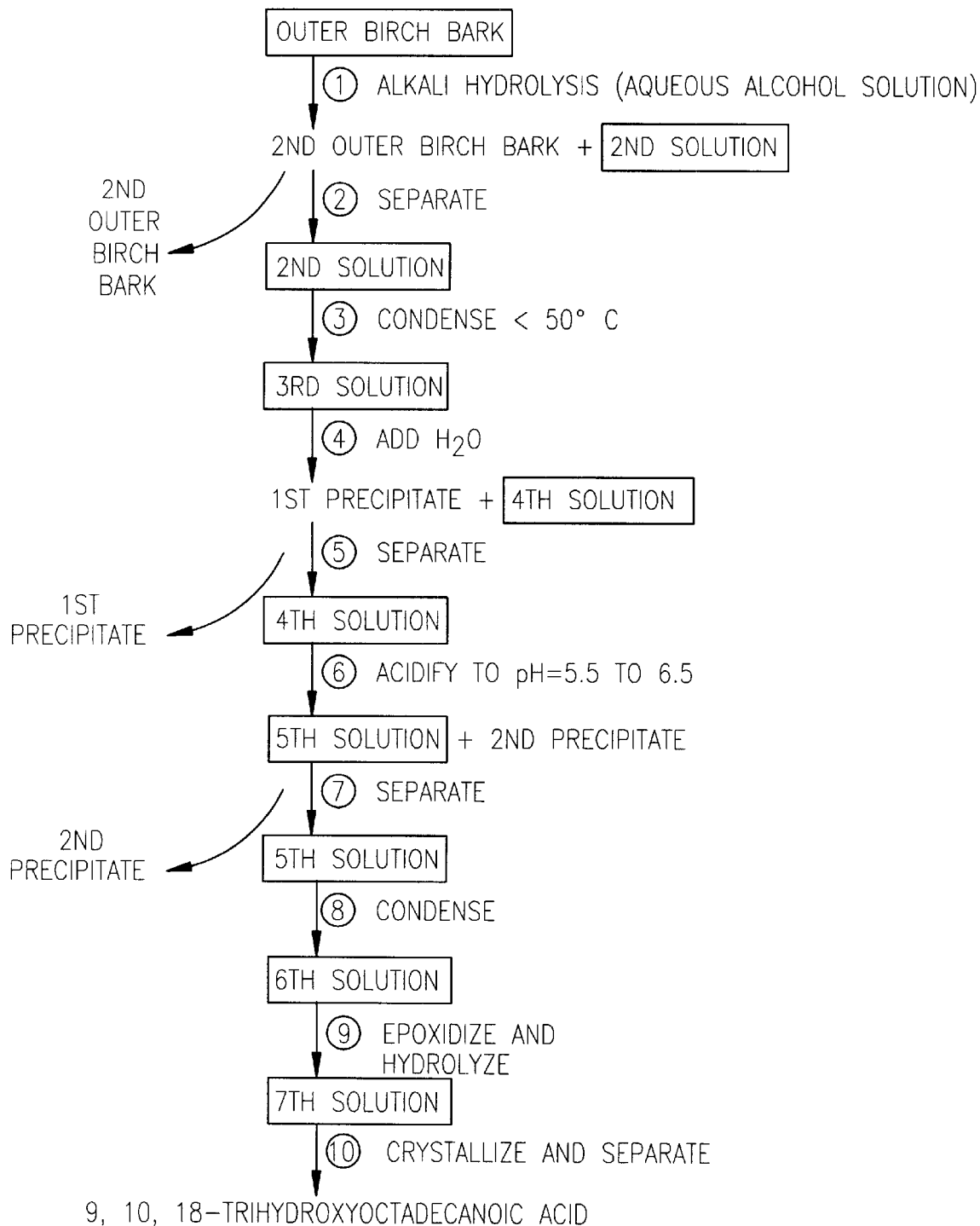
FIG. 5 is a schematic illustration of the isolation of 9,10,18-trihydroxyoctadecanoic acid from outer birch bark.

Isolation of 9,10,18-Trihydroxyoctadecanoic Acid from Outer Birch Bark (FIG. 5):

As illustrated in FIG. 5, step 1, outer birch bark is subject to alkali hydrolysis as described herein above in FIG. 4, step 1.

Lupeol and betulin are optionally removed from the outer birch bark prior to the outer birch bark being subject to alkali hydrolysis to facilitate the isolation of 9,10,18-trihydroxyoctadecanoic acid from outer birch bark.

As illustrated in FIG. 5, step 2, the second solution is separated from the second outer birch bark as described herein above in FIG. 4, step 2.

As illustrated in FIG. 5, step 3, the second solution is condensed as described hereinabove in FIG. 4, step 3 to form a third solution.

As illustrated in FIG. 5, steps 4 and 5, water is added to the third solution to form a first precipitate and a fourth solution. The first precipitate is then separated from the fourth solution as described herein above in FIG. 4, step 5.

As illustrated in FIG. 5, step 6, the fourth solution is acidified to a pH of about 5.5 to about 6.5 as described herein above in FIG. 4, step 6 to provide a fifth solution and a second precipitate.

As illustrated in FIG. 5, step 7, the second precipitate is separated from the fifth solution as disclosed herein above in FIG. 4, step 5.

The second precipitate can optionally be crystallized or precipitated from a suitable solvent (e.g., an alcohol) to give a solid and a filtrate and the solid may be separated (e.g., filtered) from the filtrate.

As illustrated in FIG. 5, step 8, the fifth solution is condensed as described herein above in FIG. 4, step 3 to provide a sixth solution.

As illustrated in FIG. 5, step 9, the sixth solution is subject to epoxidizing conditions to provide an epoxide. The epoxide is then hydrolyzed. Both reactions can conveniently be carried out in a single reaction vessel. The sixth solution is subject to epoxidizing conditions and the resulting epoxide is hydrolyzed under any suitable conditions known in the art. E. Seoane and M. Arno, Total Synthesis and Stereochemistry of Phloionolic acids, *Anales de Quimica*, 73, N11, 1336–1339 (1977). For example, the sixth solution may be epoxidized and hydrolyzed by the addition of hydrogen peroxide and an acid to the sixth solution and subsequent heating of the resulting mixture.

As illustrated in FIG. 5, Step 10, 9,10,18-trihydroxyoctadecanoic acid is crystallized from the seventh solution. The crystalline product is then separated from solution. The crystalline product may be separated from the seventh solution using any suitable technique known in the art. For example, the crystalline product can be separated from solution by filtering, hot filtering or centrifuging. Specifically, the 9,10,18-trihydroxyoctadecanoic acid is separated by filtering.

The 9,10,18-trihydroxyoctadecanoic acid can optionally be purified using any suitable technique known in the art. For example, 9,10,18-trihydroxyoctadecanoic acid can be purified by recrystallization, extraction, chromatography or sublimation. Specifically, 9,10,18-trihydroxyoctadecanoic acid can be purified by recrystallization from an aqueous alcohol solution (e.g., ethanol:water, 90:10).

Isolation of Non-Soluble Polyphenolic Polymers and Fatty Acids (FIG. 6):

As used herein, "non-soluble polyphenolic polymers" are polymers, which are non-soluble in water at a pH below about 4.0, but are typically soluble in water at a pH above about 6.0. In addition, non-soluble polyphenolic polymers are soluble in acetone, alcohols and other polar solvents.

Figure 6:
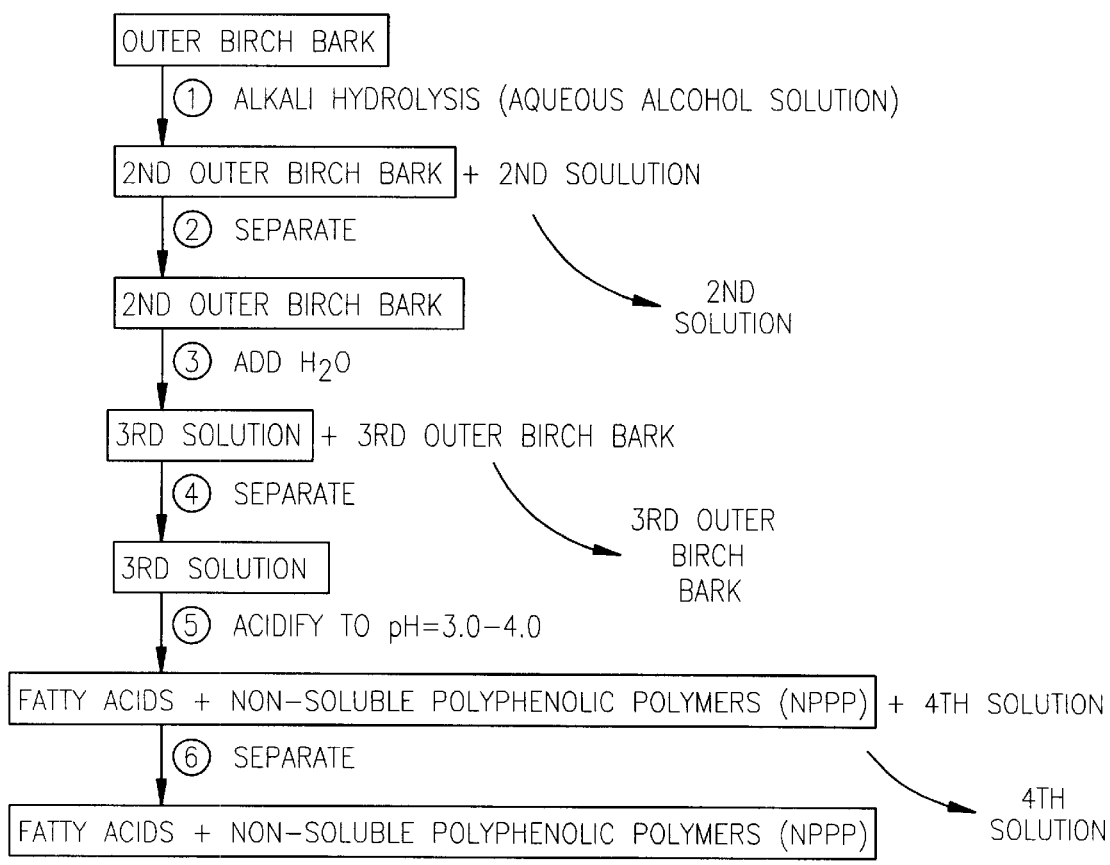
FIG. 6 is a schematic illustration of the isolation of a mixture of fatty acids and non-soluble polyphenolic polymers (NPPP) from outer birch bark.

As illustrated in FIG. 6, step 1, outer birch bark is subject to alkali hydrolysis as described herein above in FIG. 4, step 1 to provide a second birch bark and a second solution.

Lupeol and betulin are optionally removed from the outer birch bark prior to the outer birch bark being subject to alkali hydrolysis to facilitate the isolation of non-soluble polyphenolic polymers and fatty acids from outer birch bark.

As illustrated in FIG. 6, step 2, the second solution is separated from the second outer birch bark as described herein above in FIG. 4, step 2.

As illustrated in FIG. 6, step 3, water is added to the second outer birch bark to provide a third solution and a third outer birch bark.

As illustrated in FIG. 6, step 4, the third outer birch bark is separated from the third solution as described herein above in FIG. 4, step 5.

As illustrated in FIG. 6, step 5, the third solution is acidified to a pH of about 3.0 to about 4.0 to give a fourth solution and a mixture of non-soluble polyphenolic polymers and fatty acids (hereinafter "NPPP"). The pH of the solvent may be lowered by adding a suitable acid. Acceptable acids include, for example, hydrochloric acid, sulfuric acid, phosphoric acid, formic acid, hydrobromic acid, nitric acid, acetic acid and the like.

As illustrated in FIG. 6, step 6, the mixture of non-soluble polyphenolic polymers and fatty acids is separated from the fourth solution as disclosed herein above in FIG. 5, step 10.

The mixture of fatty acids and non-soluble polyphenolic polymers can be purified using any technique known in the art. For example, the mixture of non-soluble polyphenolic polymers and fatty acids can be purified by recrystallization, extraction, chromatography or sublimation.

Using the methods of the present invention, the yield of fatty acids and non-soluble polyphenolic polymer obtained is about 20 wt. % to about 40 wt. % from the outer birch bark.

Isolation of Soluble Polyphenolic Polymers and Fatty Acids from Outer Birch Bark (FIG. 7):

As used herein, "soluble polyphenolic polymer" are that portion of the polyphenolic polymer fiaction dissolved in the media under a specific set of conditions (e.g., solvent, temperature, pH, ionic strength, etc.). Specifically, soluble polyphenolic polymers are soluble in water in both acidic and basic conditions.

Figure 7:
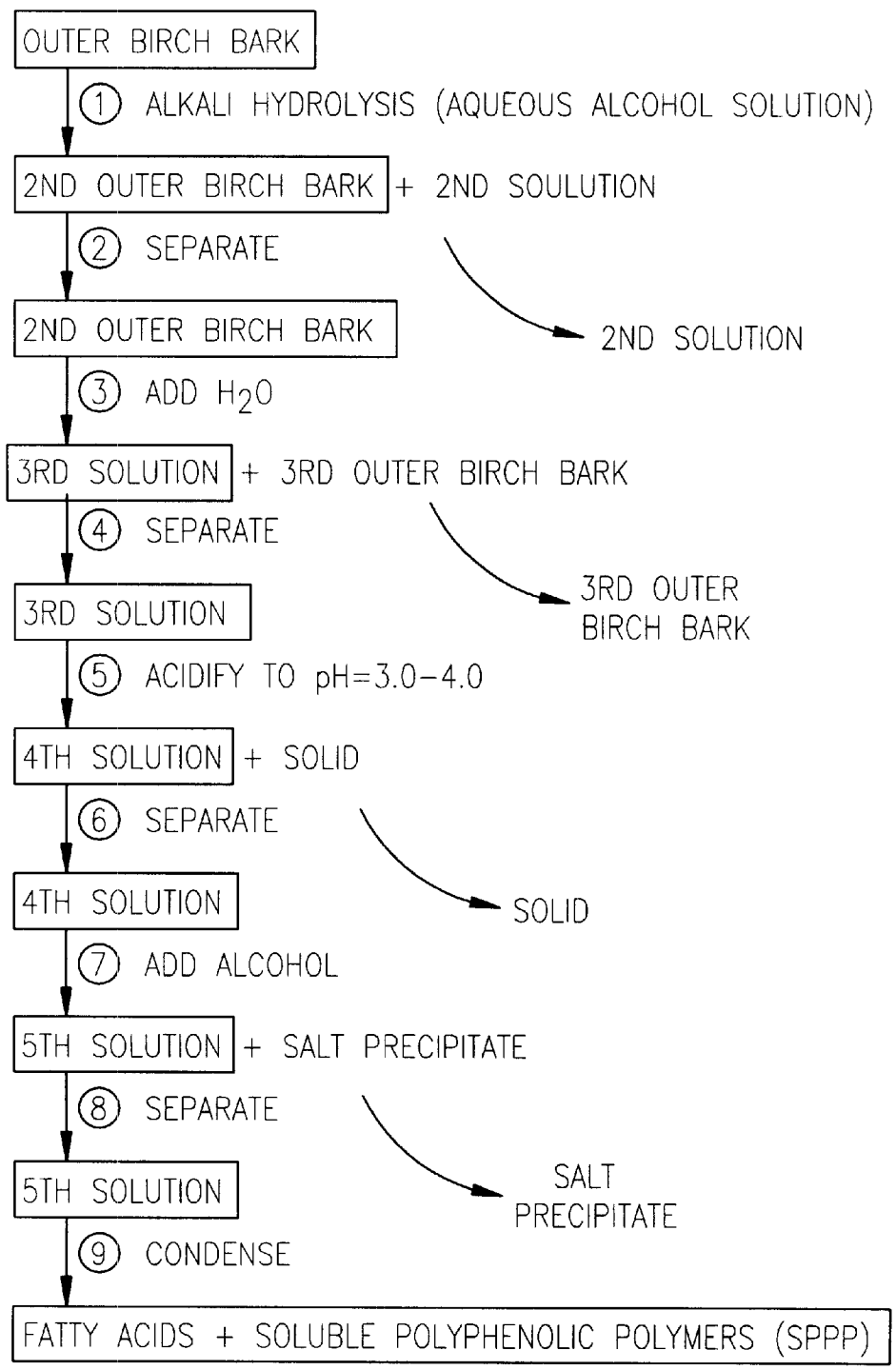
FIG. 7 is a schematic illustration of the isolation of a mixture of fatty acids and soluble polyphenolic polymers (SPPP) from outer birch bark.
Figure 8:
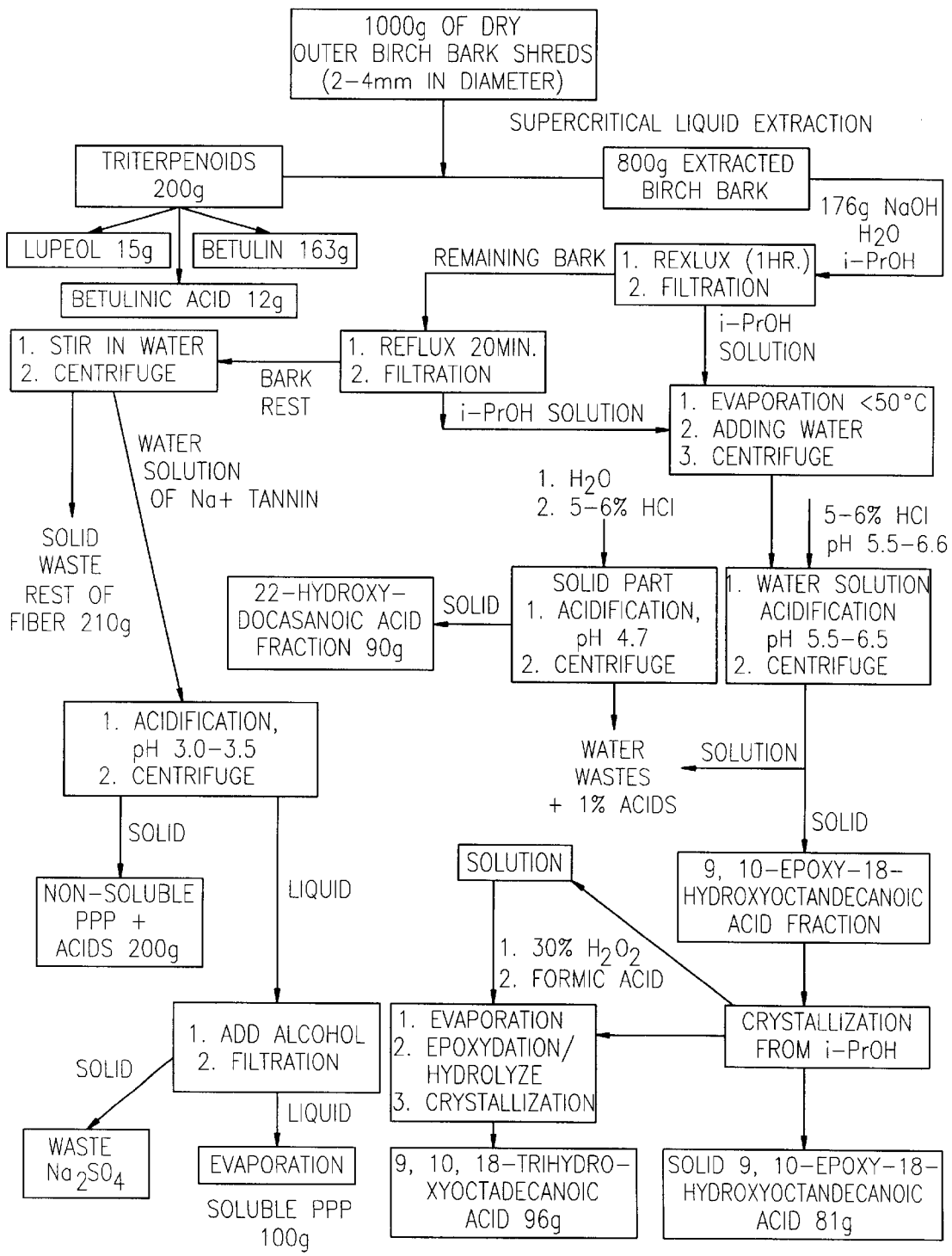
FIG. 8 is a schematic drawing of the isolation of lupeol; betulin; betulinic acid; 9,10-epoxy-18-hydroxyoctadecanoic acid; 9,10,18-trihydroxyoctadecanoic acid; a mixture of fatty acids and non-soluble polyphenolic polymers (NPPP); and a mixture of fatty acids and soluble polyphenolic polymers (SPPP) from outer birch bark.

As illustrated in FIG. 7, step 1, outer birch bark is subject to alkali hydrolysis as decsribed herein above in FIG. 4, step 1 to provide a second outer birch bark and a second solution.

Lupeol and betulin are optionally removed from the outer birch bark prior to the outer birch bark being subject to alkali hydrolysis to facilitate the isolation of soluble polyphenolic polymers and fatty acids from outer birch bark.

As illustrated in FIG. 7, Step 2, the second outer birch bark is separated from the second solution as decribed herein above in FIG. 4, step 2.

As illustrated in FIG. 7, step 3, water is added to the second outer birch bark as described herein above for FIG. 6, step 3 to provide a third outer birch bark and a third solution.

As illustrated in FIG. 7, step 4, the third solution is separated from the third outer birch bark as described herein above in FIG. 7, step 4.

As illustrated in FIG. 7, step 5, the third solution is acidified to a pH of about 3.0 to about 4.0 as described herein above in FIG. 6, step 5 to give a fourth solution and a solid.

As illustrated in FIG. 7, step 6, the solid is separated from the fourth solution as disclosed herein above in FIG. 4, step 5.

As illustrated in FIG. 7, Step 7, an alcohol is added to the fourth solution to provide a fifth solution and a precipitate.

As illustrated in FIG. 7, Step 8, the fifth solution is separated from the precipitate as disclosed herein above in FIG. 4, step 5.

As illustrated in FIG. 7, Step 9, the fifth solution is condensed as described herein above in FIG. 4, step 3 to provide a mixture of soluble polyphenolic polymers and fatty acids.

The mixture of soluble polyphenolic polymers and fatty acids can optionally be purified using any suitable technique known in the art. For example, the mixture of soluble polyphenolic polymers and fatty acids can be purified by recrystallization, extraction, chromatography or sublimation.

The yield of fatty acids and soluble polyphenolic polymers obtained from the processes of the invention is typically about 5 wt. % to about 25 wt. % from the outer birch bark. Ideally, the yield of fatty acids and soluble polyphenolic polymers obtained is about 12 wt. % to about 18 wt. % from the outer birch bark.

The present invention will be described by the following examples. The examples are for illustration purposes and do not otherwise limit the invention.

EXAMPLES

Example 1

Dry Method of Outer Birch Bark Manufacturing

Birch bark (20 kg) from a drum debarker was air dried (24 hours, room temperature) such that the water content was less than 10% and was subsequently fed into a YardMan Model 246-648D401 chipper/shredder with an 8 HP gas powered motor. The outer bark shreds and inner bark pieces (combined mass of 19.9 kg) were separated on a wire screen with openings of ¼-by-¼-inch. Outer bark shreds (approximately 5.0 to 6.0 kg) and inner bark chunks (approximately 13.0 to 14.9 kg) were recovered from the screening process. The shredded outer bark was reduced in size for extraction using a 15 BP 3B Junior Hammermill made by Jay Bee Manufacturing, Inc.

Example 2

Betulin, Betulinic Acid and Lupeol Manufacturing

Dried outer birch bark shreds (1000 g) were loaded in 5 liter fractional supercritical fluid extraction vessel. The fractional supercritical fluid extraction was conducted by Phasex Corporation, 360 Merrimack Street, Lawrence, Mass. 01843. The first supercritical fluid extraction was conducted at 45° C. and 4000 psi for two hours, employing carbon dioxide as a solvent. After which time, the first fraction (60 grams) was gathered in a separation vessel. The second supercritical fluid extraction was conducted at 90° C. and 9000 psi for 4 hours, employing carbon dioxide as a solvent. After which time, the second fraction (150 grams) was gathered in a separation vessel.

GC/MS analysis of the first fraction: 33% lupeol, 61% betulin, 2% betulinic acid, 4% other triterpenes and fatty acids.

GC/MS analysis of the second fraction: 2% lupeol, 80% betulin, 13% betulinic acid, 5% other triterpenes and fatty acids.

The first fraction (60 g) was boiled with ethanol (1.2 liters) and aluminum isopropoxide (5 g) was added. The resulting mixture was hot filtered and the filtrate was cooled at 0° C. for 3 hours. Crystals formed from solution and were filtered to afford betulin (30 g, greater than 90% pure, yield 3% from dry bark).

The above filtrate was purified on silica [eluent: hexane-ether (4:1)] employing column chromatography at atmospheric pressure. Lupeol (17 g, 1.7 wt. % on dry bark, greater than 90% pure) and betulin (5 g, greater than 90% pure, 0.5 wt. % on dry bark) were obtained.

The second fraction (150 g) was boiled with ethanol (3 liters) and aluminum isopropoxide (20 g) was added. The resulting mixture was hot filtered and the filtrate was evaporated to a volume 0.7 liters and cooled at 0° C. for 3 hours. Crystals formed from solution and were filtered to afford betulin (115 g, greater than 90% pure, yield 11.5% from dry bark).

Total yield: betulin: 3%+0.5%+11.5% =15% (from dry bark)

Total yield: lupeol: 1.7% (from dry bark)

Betulinic Acid Separation a) The solids obtained from the above hot filtration of the first fraction, ethanol, and aluminum isopropoxide were combined, washed with hot ethanol, acidified with 2% HCl, filtered, washed with hexane, washed with hexane-ether (1:1), methylated with dimethylsulfide, purified on silica [eluent: hexane-ether (4:1)] and hydrolyzed in 5% sodium hydroxide in ethanol to afford betulinic acid (16 g, greater than 95% purity, yield 1.6 wt. % on dry bark).

b) Alternatively, the solids obtained from the above hot filtration of the first fraction, ethanol, and aluminum isopropoxide were combined, washed with hot ethanol, acidified with 2% HCl, filtered, washed with hexane, washed with hexane-ether (1:1), washed with methylene chloride, and recrystallized from methanol to provide betulinic acid (14 g, greater than 90% purity, yield 1.4 wt. % on dry bark).

The betulin, betulinic acid and lupeol obtained from the methods of the present invention were identical to commercial reagents and were confirmed by m.p, IR-, $H^1$-NMR and $C^{13}$-NMR and GC/MS-spectra (from Aldrich Co., in Catalog 1997: Betulin—#12,376-5, p. 166; Betulinic Acid—#85, 505-7; from Sigma Co., in Catalog 1999, Lupeol-L 5632, p. 655).

Example 2

Alkali Hydrolysis of Birch Bark, Isolation of 22-Hydroxydocosanoic Fraction and 9,10-Epoxy-18-hydroxyoctadecanoic Acid Fraction Outer birch bark (790 g) obtained after supercritical fluid extraction was added to a solution of NaOH (176 g, 4.4 mol) in 95% isopropanol (8 liters) and the mixture was refluxed (1 hour). After hot filtration, isopropanol (3.8 liters) was added to the bark and the mixture was refluxed (20 minutes). The reaction mixture was filtered and the filtrate was evaporated in vacuo at 30° C. (GS/MC sample 1). $H_2O$ (5 liters) was added to the condensed residue and the mixture was stirred for 2 hours at room temperature. The insoluble material was separated by centrifugation and acidified with 6% HCl to pH=4.7 (GS/MC sample 2) to afford 22-hydroxydocosanoic (90 g). The purity of the 22-hydroxydocasanoic by GC/MS analysis is greater than 50%. The water solution after centrifugation (i.e., supernatant) was acidified with 6% HCl to pH=5.5–6.5 and the 9,10-epoxy-18-hydroxyoctadecanoic acid fraction (179 g) was obtained by filtration. The purity of 9,10-epoxy-18-hydroxyoctadecanoic fraction by GC/MS analysis is greater than 70%.

Example 3

Recrystallization of 9,10-Epoxy-18-hydroxyoctadecanoic Acid 9,10-Epoxy-18-hydroxyoctadecanoic acid (179 g) was added to isopropanol (1.7 liters) and the mixture was allowed to reflux until all of the acid was dissolved. The temperature of the solution was decreased to room temperature and precipitation occurred over a period of approximately 5 hours. After centrifuging, the solution was evaporated and the resulting solid was crystallized in isopropanol (1 liter). The combined solids were dried in vacuo and 9,10-epoxy-18-hydroxyoctadecanoic acid (81 g) was obtained. The purity is greater than 95% (GC/MS analysis).

Example 4

Isolation of 9,10,18-Trihydrohyoctadecanoic Acid (Pholiolic Acid)

The supernatant from Example 3 was evaporated and added to a solution of 30% $H_2O_2$ (164 ml, 1.4 mol $H_2O_2$) in 95% formic acid (1.3 liters) and stirred for 3 hours at 40° C. The mixture was evaporated in vacuo and a solution of 10% NaOH was added (to pH=9.0). The solution was stirred for 1 hour at 60° C. and 6% aqueous HCl solution was added dropwise to the stirring mixture (to pH=5.5). The resulting solids were separated by centrifugation, and dried in vacuo. The solids were crystallized from ethanol-water (4/1) to afford 9,10,18-trihydrohyoctadecanoic acid (96 g). The purity is greater than 95% (GC/MS analysis).

Example 5

Polyphenolic Polymer and Fatty Acids Separation

The remaining bark (57 g) from alkaline hydrolysis in Example 2 was added to water (7 liters) and stirred for 2 hours. The remaining solids (112 g) were separated by centrifugation and the aqusous solution was acidified with 37% HCl (to pH=3.0). The resulting mixture of non-soluble polyphenolic polymers (200 g) and fatty acids was isolated via centrifugation. The aqueous solution separated during centrifuigation was evaporated to a volume of 1 liter and ethanol (3 liters) was added. The solvent was evaporated and a mixture of fatty acids and soluble polyphenolic polymer (SPPP) was obtained. Yield 105 g (10 wt. %) on dry bark.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A process for separating outer birch bark from inner birch bark comprising subjecting birch bark to fragmentation to provide a combination of outer birch bark shreds and inner birch bark chunks and separating the outer birch bark shreds from the inner birch bark chunks.

2. The process of claim 1 wherein the separating comprises pushing the outer birch bark shreds through a mesh effective to separate the outer birch bark shreds from the inner birch bark chunks or the separating is accomplished with the use of an air classifier.

3. The process of claim 1 or 2 wherein the fragmentation is accomplished with a chipper or a shredder.

4. The process of claim 1 or 2 further comprising reducing the size of the outer birch bark shreds with the use of a hammermill.

* * * * *

UNITED STATES PATENT AND TRADEMARK OFFICE
CERTIFICATE OF CORRECTION

PATENT NO. : 6,634,575 B2
DATED : October 21, 2003
INVENTOR(S) : Krasutsky et al.

It is certified that error appears in the above-identified patent and that said Letters Patent is hereby corrected as shown below:

Title page,
Item [75], Inventors, delete "Robert M. Carlson, Duluth, MN (US);" and delete "Vitaliy V. Nesterenko, Duluth, MN (US);".
Item [62], Related U.S. Application Data, delete "09/371,298" and insert -- 07/371,298 --, therefor.
Item [56], References Cited, U.S. PATENT DOCUMENTS, insert -- 241/21 -- after "Berlyn et al."; insert -- * -- after "3,981,453 A" and delete "241/119" and insert -- 241/19 --, therefor.
OTHER PUBLICATIONS, "Schweizer, P., et al.," reference, delete "aagainst" and insert -- against --, therefor.

Drawings,
Sheet 7 of 10, Fig. 6, delete "SOULUTION" and insert -- SOLUTION --, therefor.
Sheet 8 of 10, Fig. 7, delete "SOULUTION" and insert -- SOLUTION --, therefor.

Column 1,
Line 8, delete "09/371,298" and insert -- 07/371,298 --, therefor.

Column 2,
Line 42, delete "anti-fingal" and insert -- anti-fungal --, therefor.
Line 54, delete "Holzforsch" and insert -- Holzforschung --, therefor.

Column 3,
Line 26, delete "verucosa" and insert -- verrucosa --, therefor.

Column 10,
Line 40, delete "100°" and insert -- 100°C --, therefor.

Column 12,
Line 47, delete "usefuil" and insert -- useful --, therefor.

Column 13,
Line 51, delete "the" before "oxirane".

Column 15,
Line 35, delete "fiaction" and insert -- fraction --, therefor.

Column 16,
Line 33, delete "6.0 kg" and insert -- 6.9 kg --, therefor.

UNITED STATES PATENT AND TRADEMARK OFFICE
CERTIFICATE OF CORRECTION

PATENT NO.    : 6,634,575 B2
DATED         : October 21, 2003
INVENTOR(S)   : Krasutsky et al.

It is certified that error appears in the above-identified patent and that said Letters Patent is hereby corrected as shown below:

Column 16 (cont'd),
Line 36, delete "15 BP" and insert -- 15 HP --, therefor.
Line 45, delete "Mass" and insert -- MA --, therefor.

Signed and Sealed this

Eighth Day of June, 2004

JON W. DUDAS
*Acting Director of the United States Patent and Trademark Office*